US008393896B2

(12) United States Patent
Oda

(10) Patent No.: US 8,393,896 B2
(45) Date of Patent: Mar. 12, 2013

(54) SELF-LIGATING ORTHODONTIC BRACKET

(75) Inventor: Todd I. Oda, Torrance, CA (US)

(73) Assignee: Ormco Corporation, Orange, CA (US)

( * ) Notice: Subject to any disclaimer, the term of this patent is extended or adjusted under 35 U.S.C. 154(b) by 0 days.

(21) Appl. No.: 13/052,759

(22) Filed: Mar. 21, 2011

(65) Prior Publication Data
US 2011/0195372 A1 Aug. 11, 2011

Related U.S. Application Data

(63) Continuation of application No. 11/837,169, filed on Aug. 10, 2007, now Pat. No. 7,909,603, and a continuation of application No. 11/032,977, filed on Jan. 11, 2005, now Pat. No. 7,267,545.

(51) Int. Cl.
A61C 3/00 (2006.01)
(52) U.S. Cl. ........................................................ 433/10
(58) Field of Classification Search ................ 433/8–17
See application file for complete search history.

(56) References Cited

U.S. PATENT DOCUMENTS

| 2,549,528 | A | 4/1951 | Russell |
| 3,772,787 | A | 11/1973 | Hanson |
| 4,248,588 | A | 2/1981 | Hanson |
| 4,492,573 | A | 1/1985 | Hanson |
| 4,559,012 | A | 12/1985 | Pletcher |
| 4,820,151 | A | 4/1989 | Pospisil |
| 4,927,362 | A | 5/1990 | Snead |
| 5,094,614 | A | 3/1992 | Wildman |
| 5,248,257 | A | 9/1993 | Cannon |
| 5,254,002 | A | 10/1993 | Reher et al. |
| 5,275,557 | A | 1/1994 | Damon |
| 5,322,435 | A | 6/1994 | Pletcher |
| 5,429,500 | A | 7/1995 | Damon |
| 5,439,378 | A | 8/1995 | Damon |
| 5,466,151 | A * | 11/1995 | Damon ........................... 433/10 |
| 5,474,445 | A | 12/1995 | Voudouris |
| 5,474,446 | A | 12/1995 | Wildman et al. |
| 5,562,444 | A | 10/1996 | Heiser et al. |
| 5,586,882 | A | 12/1996 | Hanson |
| 5,613,850 | A | 3/1997 | Wildman et al. |

(Continued)

FOREIGN PATENT DOCUMENTS

| EP | 0 623 320 A1 | 11/1994 |
| EP | 0691106 A1 | 1/1996 |

(Continued)

OTHER PUBLICATIONS

European Patent Office, Office Action in European Application No. 08012705.3-2318 dated Mar. 3, 2011.

(Continued)

Primary Examiner — Cris L Rodriguez
Assistant Examiner — Eric Rosen
(74) Attorney, Agent, or Firm — Wood, Herron & Evans, LLP

(57) ABSTRACT

An orthodontic bracket having a bracket body configured to be mounted to a tooth includes an archwire slot having a base surface defining a base plane and a slide engagement track defining a translation plane. The translation plane is angled with respect to the base plane. A ligating slide is engaged with the slide engagement track of the bracket body and movable along the slide engagement track and parallel to the translation plae between an opened position, in which an archwire is insertable into the archwire slot, and a closed position, in which the archwire is retained within the archwire slot. The translation plane is angled with respect to the base plane so as to prevent the ligating slide from contacting the gingiva surrounding the tooth when the ligating slide is moved to the opened position.

26 Claims, 4 Drawing Sheets

U.S. PATENT DOCUMENTS

| | | |
|---|---|---|
| 5,630,715 A | 5/1997 | Voudouris |
| 5,630,716 A | 5/1997 | Hanson |
| 5,685,711 A | 11/1997 | Hanson |
| 5,711,666 A | 1/1998 | Hanson |
| 5,857,850 A | 1/1999 | Voudouris |
| 5,906,486 A | 5/1999 | Hanson |
| 5,908,293 A | 6/1999 | Voudouris |
| 5,913,680 A | 6/1999 | Voudouris |
| 6,071,118 A | 6/2000 | Damon |
| 6,071,119 A | 6/2000 | Christoff et al. |
| 6,142,775 A | 11/2000 | Hansen et al. |
| 6,168,428 B1 | 1/2001 | Voudouris |
| 6,193,508 B1 | 2/2001 | Georgakis |
| 6,206,690 B1 | 3/2001 | Vargas |
| 6,247,923 B1 | 6/2001 | Vashi |
| 6,257,883 B1 | 7/2001 | Voudouris |
| 6,358,045 B1 | 3/2002 | Farzin-Nia et al. |
| 6,364,659 B1 | 4/2002 | Lotte |
| 6,428,314 B1 | 8/2002 | Jones, Jr. et al. |
| 6,485,299 B1 | 11/2002 | Wildman |
| 6,506,049 B2 | 1/2003 | Hanson |
| 6,607,383 B2 | 8/2003 | Abels et al. |
| 6,616,445 B2 | 9/2003 | Abels et al. |
| 6,655,957 B2 | 12/2003 | Abels et al. |
| 6,655,958 B2 | 12/2003 | Abels et al. |
| 6,659,766 B2 | 12/2003 | Abels et al. |
| 6,659,767 B2 | 12/2003 | Abels et al. |
| 6,695,612 B2 | 2/2004 | Abels et al. |
| 6,709,268 B2 | 3/2004 | Pospisil et al. |
| 6,733,286 B2 | 5/2004 | Abels et al. |
| 6,776,613 B2 | 8/2004 | Orikasa |
| 6,893,257 B2 | 5/2005 | Kelly |
| 6,957,957 B2 | 10/2005 | Pospisil |
| 7,267,545 B2 | 9/2007 | Oda |
| 7,419,375 B2 | 9/2008 | Farzin-Nia et al. |
| 7,909,603 B2 * | 3/2011 | Oda .................. 433/24 |
| 2001/0005574 A1 | 6/2001 | Manemann et al. |
| 2002/0098460 A1 | 7/2002 | Farzin-Nia et al. |
| 2002/0119414 A1 | 8/2002 | Orikasa |
| 2004/0014005 A1 * | 1/2004 | Kuhn ................. 433/127 |
| 2004/0072117 A1 | 4/2004 | Farzin-Nia et al. |
| 2004/0086826 A1 | 5/2004 | Pospisil |
| 2004/0121279 A1 | 6/2004 | Kelly |
| 2004/0166458 A1 | 8/2004 | Opin et al. |

FOREIGN PATENT DOCUMENTS

| | | |
|---|---|---|
| GB | 687226 A | 2/1953 |
| JP | 08168497 A | 7/1996 |
| JP | 2003061980 A | 3/2003 |
| WO | 2004/047665 A1 | 6/2004 |
| WO | 2005/002461 A1 | 1/2005 |

OTHER PUBLICATIONS

European Patent Office, Partial European Search Report in Corresponding European Application No. EP 05 25 8116, dated Aug. 4, 2006 (11 pages).

Japanese Patent Office, Office Action in Japanese Patent Application No. JP2006-003007, mailed Mar. 17, 2009; 7 pages.

European Patent Office; Claudio Salvatore; European Search Report issued in corresponding European Application No. EP 10177158.2; Nov. 17, 2010; 6 pages.

European Patent Office; Claudio Salvatore; Partial European Search Report issued in corresponding European Application No. EP 08012705, dated Oct. 10, 2008; 8 pages.

U.S. Patent and Trademark Office, Office Action in U.S. Appl. No. 11/837,169, dated Dec. 29, 2008.

U.S. Patent and Trademark Office, Office Action in U.S. Appl. No. 11/837,169, dated Sep. 29, 2009.

U.S. Patent and Trademark Office, Office Action in U.S. Appl. No. 11/837,169, dated Apr. 16, 2010.

U.S. Patent and Trademark Office, Office Action in U.S. Appl. No. 11/837,169, dated Sep. 2, 2010.

U.S. Patent and Trademark Office, Office Action in U.S. Appl. No. 11/032,977, dated Sep. 22, 2006.

European Patent Office, Partial European Search Report in Corresponding European Application No. EP 05 25 8116, dated May 4, 2006 (4 pages).

Japanese Patent Office, Office Action in Japanese Patent Application No. JP2006-003007, mailed Oct. 6, 2009; 4 pages.

Japanese Patent Office, Office Action in Japanese Patent Application No. JP2006-003007, mailed May 6, 2010; 4 pages.

* cited by examiner

SELF-LIGATING ORTHODONTIC BRACKET

CROSS-REFERENCE TO RELATED APPLICATIONS

This application is a continuation of U.S. application Ser. No. 11/837,169 filed Aug. 10, 2007, which is a continuation of U.S. application Ser. No. 11/032,977 filed Jan. 11, 2005, now U.S. Pat. No. 7,267,545, the disclosures of which are incorporated by reference herein in their entireties.

FIELD OF THE INVENTION

The invention relates generally to orthodontic brackets and, more particularly, to self-ligating orthodontic brackets.

BACKGROUND OF THE INVENTION

Orthodontic brackets represent a principal component of all corrective orthodontic treatments devoted to improving a patient's occlusion. In conventional orthodontic treatments, an orthodontist or an assistant affixes brackets to the patient's teeth and engages an archwire into a slot of each bracket. The archwire applies corrective forces that coerce the teeth to move into correct positions. Traditional ligatures, such as small elastomeric O-rings or fine metal wires, are employed to retain the archwire within each bracket slot. Due to difficulties encountered in applying an individual ligature to each bracket, self-ligating orthodontic brackets have been developed that eliminate the need for ligatures by relying on a movable portion or member, such as a latch or slide, for captivating the archwire within the bracket slot.

Conventional orthodontic brackets for the first and second molar teeth typically include a bracket in the form of a buccal tube that provides an anchor for the archwire. The buccal tube is typically secured to a tooth or to a molar band, which is in turn cemented to the first or second molar teeth. A terminal end of a conventional archwire is then fitted into the tube to facilitate orthodontic treatment. In some orthodontic treatments, a severely rotated molar makes it difficult to insert the end of the archwire into both the first and second molar tubes. In these severely rotated cases, a convertible buccal tube is often used on the first molar tooth to overcome the difficulty encountered with conventional buccal tubes.

In some orthodontic treatments, however, it is undesirable to fix the archwire and prevent movement of the archwire, as is done when traditional ligatures secure the archwire to a convertible buccal tube. To overcome this limitation of current molar brackets, it would be desirable to use self-ligating brackets on the first and/or second molars. Nevertheless, their use has heretofore presented some undesirable drawbacks. For instance, one problem in using self-ligating brackets on the molar teeth is that their size often creates occlusion problems between the bracket and teeth on the opposing jaw. As the upper and lower teeth are brought together, such as for example, during chewing, the upper teeth may contact the brackets on the lower molars and may break or dislodge the brackets therefrom.

Furthermore, under normal conditions the gingival-occlusal height of molar teeth provides a limited surface on which to mount an orthodontic bracket. Prior self-ligating brackets have slides that engage the bracket body from below and travel along guides in the bracket body that are substantially parallel to the gingival-occlusal plane. Moreover, when in an opened position, the bottom edge of the slide extends below the bracket body. Thus, if traditional self-ligating brackets were attached to the bottom molar teeth, the bottom edge of the slide would contact gum tissue (gingival) causing patient discomfort. Moreover, because gingival interference with the slide would be significant, the slide could not be fully opened to accept an archwire thus defeating an advantage of self-ligating brackets.

Yet another problem often encountered with traditional direct bonded self-ligating brackets is with applying the brackets to teeth. To apply a self-ligating bracket to a tooth, a medical practitioner will use a tool, such as tweezers, to grasp the bracket and manipulate the bracket within the oral cavity. Traditional self-ligating brackets, however, typically do not provide convenient gripping points so that the medical practitioner may securely grasp the bracket. Consequently, it is difficult to manipulate the bracket within the oral cavity without the bracket disengaging from the tweezers and falling on the floor or in a patient's mouth. This problem would be exacerbated when attempting to apply self-ligating brackets to molar teeth at the rear of the oral cavity.

There is a need for a self-ligating orthodontic bracket attachable to molar teeth that overcomes these and other deficiencies of conventional self-ligating orthodontic brackets.

SUMMARY OF THE INVENTION

In one aspect of the invention, an orthodontic bracket includes a bracket body configured to be mounted to a tooth and includes an archwire slot having a base surface generally defining a base plane. The bracket body further includes a slide engagement track generally defining a translation plane. The translation plane is acutely angled with respect to the base plane. A ligating slide is engaged with the slide engagement track of the bracket body and movable along the slide engagement track and parallel to the translation plane between an opened position, in which an archwire is insertable into the archwire slot, and a closed position, in which the archwire is retained within the archwire slot. The translation plane may be angled between approximately 10 degrees and approximately 25 degrees, and preferably approximately 20 degrees, with respect to the base plane. The angled relation between the translation plane and the base plane is configured to prevent the ligating slide from contacting the gingiva surrounding the tooth when the ligating slide is moved to the opened position.

To provide a close fit between the archwire and the archwire slot, the ligating slide includes a surface confronting the slide engagement track having a first and second portion. The first portion engages the slide engagement track. The second portion covers the archwire slot when the ligating slide is in the closed position and is angled with respect to the first portion so that the second portion is generally parallel to the base plane.

In another aspect of the invention, the bracket body includes a confronting side adapted to face teeth on an opposite jaw. The confronting side has a contoured shape such that as the jaws are closed and the upper and lower teeth are brought together, there is no occlusal interference between the orthodontic bracket and the teeth in the opposite jaw. The confronting side may include a recess adjacent an outer end that defines a generally planar surface which is substantially orthogonal to the base plane. The planar surface is adapted to provide a gripping point for an orthodontic tool, such as tweezers, used to apply the bracket to the tooth.

In yet another aspect of the invention, the movement of the ligating slide relative to the bracket body may be restricted so as to prevent the ligating slide from disengaging the bracket body. The bracket body may include one of a projecting portion or a receiving portion and the ligating slide may include the other of the projecting portion and the receiving portion, wherein the projecting portion or receiving portion moves relative to the other as the ligating slide moves along the slide engagement track between the opened and closed positions. The receiving portion includes a first end configured such that the projecting portion engages the first end when the ligating slide is in the opened position. In this way, the ligating slide is prevented from accidently or inadvertently disengaging from the bracket body.

In one embodiment, a retaining pin projects from the slide engagement track and the ligating slide includes a retaining slot extending through the ligating slide and oriented in a direction along which the ligating slide moves between the opened and closed positions. The retaining pin is received within the retaining slot and the retaining slot moves relative to the retaining pin as the ligating slide moves between the opened and closed positions. Another embodiment further shows the retaining pin associated with the ligating slide and a retaining groove associated with the bracket body that operates in a similar manner as described above. Other configurations are also possible for restricting the movement of the ligating slide relative to the bracket body. For instance, in other embodiments of the invention, the slide engagement track is bounded by at least one side wall having one of a projecting portion or a receiving portion and the ligating slide includes a peripheral edge that confronts the side wall. The peripheral edge includes the other of the projecting portion or the receiving portion. The projecting portion may be, for example, a retaining pin or a retaining ball and the receiving portion may be a retaining groove.

The above and other objects and advantages of the invention shall be made apparent from the accompanying drawings and the description thereof.

BRIEF DESCRIPTION OF THE DRAWINGS

The accompanying drawings, which are incorporated in and constitute a part of this specification, illustrate embodiments of the invention and, together with a general description of the invention given above, and the detailed description of the embodiments given below, serve to explain the principles of the invention.

DETAILED DESCRIPTION

Although the invention will be described next in connection with certain embodiments, the invention is not limited to practice in any one specific type of self-ligating orthodontic bracket. The description of the embodiments of the invention is intended to cover all alternatives, modifications, and equivalent arrangements as may be included within the spirit and scope of the invention as defined by the appended claims. In particular, those skilled in the art will recognize that the components of the embodiments of the invention described therein could be arranged in multiple different ways.

Figure 1:
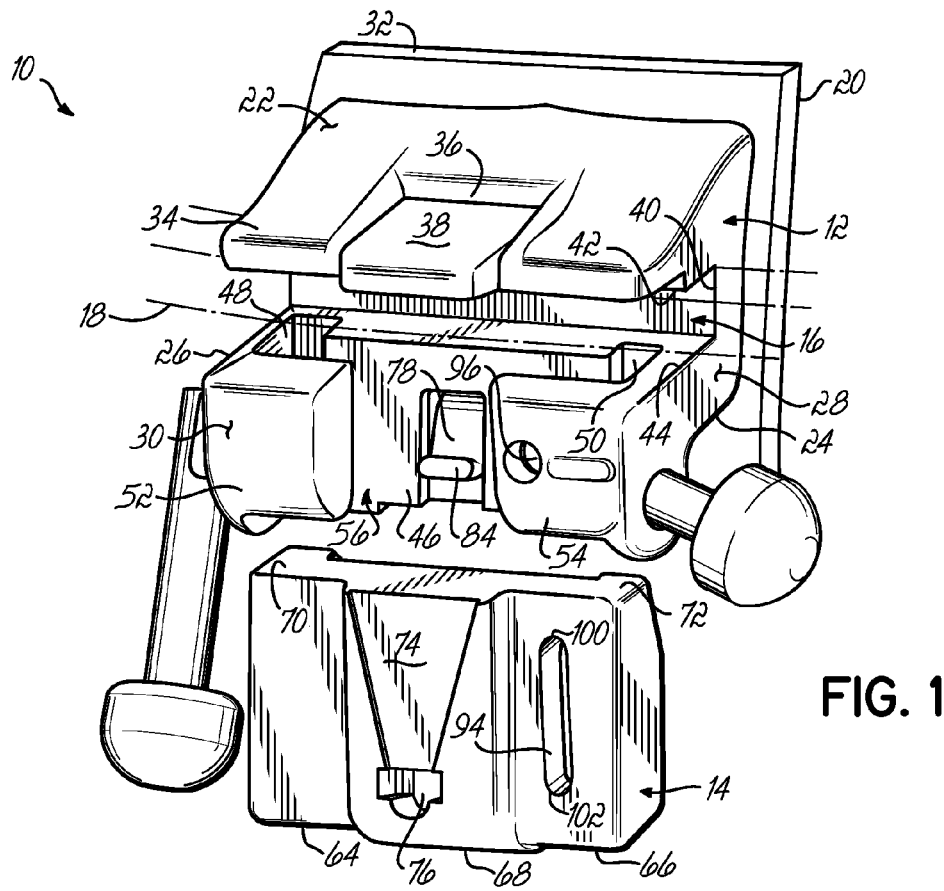
FIG. 1 is a perspective view of a self-ligating orthodontic bracket according to the invention in which the ligating slide is removed from the assembly for clarity.
Figure 2:
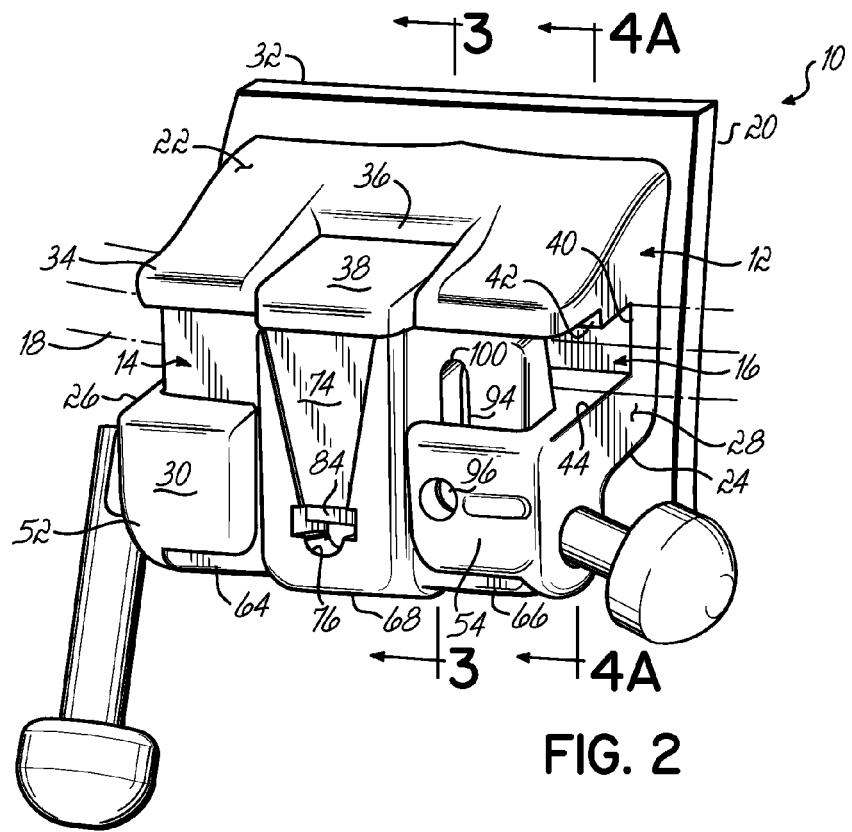
FIG. 2 is a perspective view of the self-ligating orthodontic bracket of FIG. 1 with the ligating slide in the closed position.

With reference to FIGS. 1 and 2, an orthodontic bracket, generally indicated by reference numeral 10, includes a bracket body 12 and a movable ligating slide 14 slidably coupled with the bracket body 12. The bracket body 12 includes an archwire slot 16 formed therein adapted to receive an archwire 18 (shown in phantom). The ligating slide 14 is moveable between an opened position in which the archwire 18 is insertable into the archwire slot 16 and a closed position in which the archwire 18 is retained within the archwire slot 16. The bracket body 12 and ligating slide 14 collectively form an orthodontic bracket 10 structure for use in corrective orthodontic treatments. The invention is advantageous for self-ligating brackets placed on the first and/or second molar teeth, although not so limited.

More particularly, the invention is advantageous for self-ligating brackets placed on the first and/or second molar teeth of the lower jaw. For this reason, the orthodontic bracket 10 of the invention is described herein using a reference frame attached to a molar tooth of the lower jaw. Consequently, and as used herein, terms such as labial, lingual, mesial, distal, occlusal, and gingival used to describe bracket 10 are relative to the chosen reference frame. The invention, however, is not limited to the chosen reference frame and descriptive terms, as the orthodontic bracket 10 of the invention may be used on other teeth and in other orientations within the oral cavity. By way of example, the orthodontic bracket 10 may be used on the molar teeth in the upper jaw and oriented so that the ligating slide 14 opens in either the occlusal or gingival direction. Those of ordinary skill in the art will recognize that the descriptive terms used herein may not directly apply when there is a change in reference frame. Nevertheless, the invention is intended to be independent of location and orientation within the oral cavity and the relative terms used to describe orthodontic bracket 10 are to merely provide an adequate description of the invention. As such, the relative terms labial, lingual, mesial, distal, occlusal, and gingival are in no way limiting the invention to a particular location or orientation.

The bracket body 12 has a lingual side 20, an occlusal side 22 when mounted to a tooth 23 carried by the patient's lower jaw, a gingival side 24, a mesial side 26, a distal side 28, and a labial side 30. The lingual side 20 of the bracket body 12 is configured to be secured to tooth 23 in any conventional manner, for example, by an appropriate orthodontic cement or adhesive or by a band around an adjacent tooth. The lingual side 20 may further be provided with a pad 32 that is secured to the outer surface of tooth 23.

Figure 3:
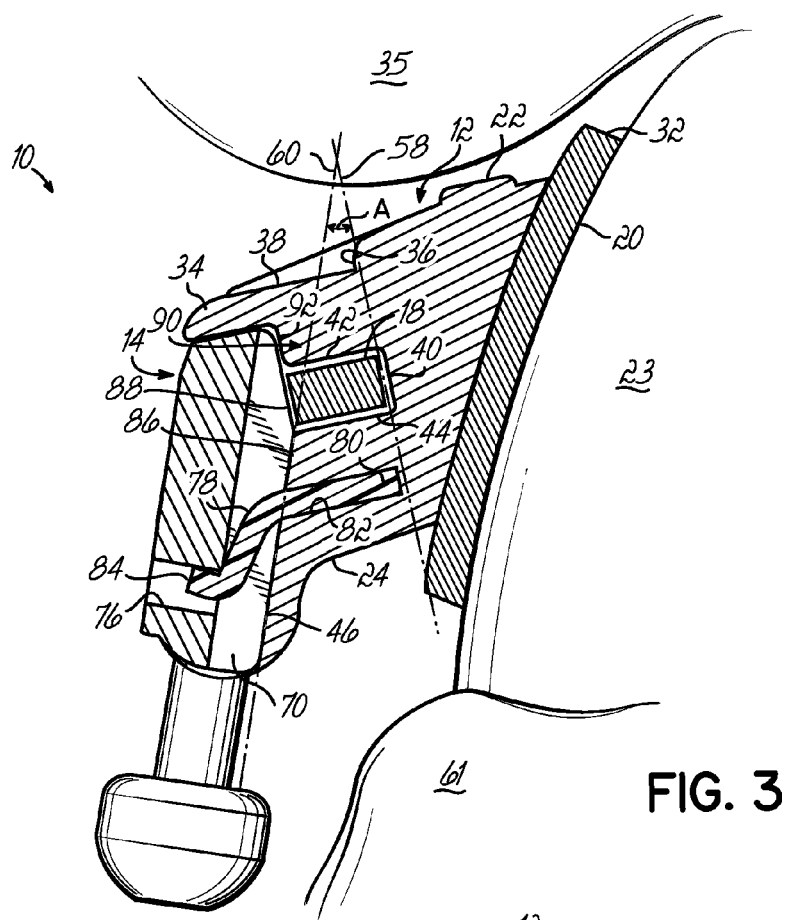
FIG. 3 is a cross-sectional view of the self-ligating orthodontic bracket of FIG. 2 generally taken along line 3-3.

In one advantageous aspect of the invention, the occlusal side 22 is profiled or contoured by including a labial portion 34 that projects generally in the gingival-labial direction. For instance, the occlusal side 22 may include a convex portion adjacent the lingual side 20 with a concave portion extending therefrom in the labial direction. In this way, the thickness of the bracket body 12 between the archwire slot 16 and occlusal side 22 is relatively thicker along the convex portion and thins or is reduced along the concave portion. Many traditional self-ligating brackets have an occlusal side that projects primarily in the labial direction. Consequently, when traditional self-ligating brackets are positioned on molar teeth, teeth on the opposing jaw often contact the occlusal side of the brackets when the teeth are brought together, such as for example during chewing. To avoid the undesirable contact of teeth with the orthodontic bracket, the self-ligating bracket 10 of the invention includes an occlusal side 22 with a labial portion 34 that projects in the gingival direction as well. This profiling moves the occlusal side 22 away from the teeth on the opposing jaw, shown schematically at 35, so that as the teeth 23, 35 are brought together, the teeth 35 on the opposing jaw do not contact the occlusal side 22 of the orthodontic bracket 10, thereby preventing occlusal interference (FIG. 3).

Occlusal side 22 may further include recess 36 in labial portion 34. Recess 36 may be advantageously configured to include a generally planar surface 38 adapted to be a gripping point for a tool (not shown), such as tweezers, for manipulating the orthodontic bracket 120 within the oral cavity. As discussed below, planar surface 38 is generally orthogonal to the base plane defined by the base of the archwire slot 16. This is particularly advantageous when attaching orthodontic brackets to molar teeth at the back of the oral cavity, where it can be difficult to manipulate the bracket 10 so as to properly attach the bracket 10 to the molar teeth 23. Many traditional self-ligating brackets include occlusal sides that are irregular and thus are not conducive to gripping by an instrument such as tweezers. To aid the medical practitioner in applying the self-ligating bracket 10 of the invention, planar surface 38 is provided within recessed area 36. Planar surface 38 provides an enhanced surface for securely gripping the orthodontic bracket 10 so that the medical practitioner may easily position the bracket 10 on the molar tooth 23.

With continued reference to FIGS. 1 and 2, the bracket body 12 includes a base surface 40 and a pair of opposed slot surfaces 42, 44, respectively, projecting labially from the base surface 40 that collectively define the archwire slot 16 extending in a mesial/distal direction from mesial side 26 to distal side 28. The slot surfaces 42, 44 and base surface 40 are substantially encapsulated or embedded within the material of the bracket body 12. The archwire slot 16 of the bracket body 12 is designed to receive the orthodontic archwire 18 in the same manner as typical prior art self-ligating orthodontic brackets.

The bracket body 12 further includes a generally planar support surface 46 projecting in a generally labial-gingival direction from slot surface 44. Support surface 46 may include a pair of slide grooves 48, 50 extending in the occlusal-gingival direction at opposed mesial-distal ends of support surface 46. A pair of opposed guides 52, 54 are carried by support surface 46 and are positioned on respective mesial and distal sides 26, 28 thereof. The guides 52, 54 are generally L-shaped each having a first leg projecting from support surface 46 in the labial direction. Guide 52 has a second leg projecting in the distal direction while guide 54 has a second leg projecting in the mesial direction so that collectively, guides 52, 54 partially overlie support surface 46. Planar support surface 46 including grooves 48, 50 and guides 52, 54 collectively define a slide engagement track 56 for supporting and guiding ligating slide 14 within bracket body 12.

In another advantageous aspect of the invention, the slide engagement track 56 and the archwire slot 16 generally have a non-orthogonal relationship. In particular, the base surface 40 of the archwire 16 generally defines a base plane 58 and the slide engagement track 56 generally defines a translation plane 60 along which the ligating slide 14 moves between the opened and closed positions. It should be recognized that base surface 40 and slide engagement track 56 need not be precisely planar but be configured such that base plane 58 and translation plane 60 may be generally defined. The base plane 58 and translation plane 60 are acutely angled with respect to each other by an angle A, as shown in FIG. 3. In this way, as the ligating slide 14 is moved from the closed position to the opened position along slide engagement track 56 and parallel to translation plane 60, the ligating slide 14 moves generally in the labial-gingival direction so that the edge of the ligating slide 14 does not make contact with the gingiva 61 adjacent orthodontic bracket 10 when mounted to molar teeth 23. To prevent the ligating slide 14 from contacting the gingiva 61, the base plane 58 and translation plane 60 have an angle A between approximately 10 degrees and approximately 25 degrees, and preferably approximately 20 degrees. The invention, however, is not so limited and, as recognized by those of ordinary skill in the art, other angles suitable for a particular application are possible.

The ligating slide 14 is a generally planar structure comprising a mesial portion 64, a distal portion 66, and a central portion 68 intermediate the mesial portion 64 and the distal portion 66. Mesial and distal portions 64 and 66 include integral slide rails 70, 72 extending in the occlusal-gingival direction and adapted to engage slide grooves 48, 50 of bracket body 12 when ligating slide 14 is engaged with bracket body 12. Additionally, guides 52, 54 overlie mesial and distal portions 64, 66 respectively, and central portion 68 projects in the labial direction such that the labial surface of central portion 68 is substantially flush with the labial side 30 of bracket body 12. The labial surface of central portion 68 may include a channel 74 that tapers or narrows in the occlusal-gingiva direction and includes an aperture 76 located near the apex of channel 74. As will be explained below, aperture 76 helps secure ligating slide 14 in the closed position.

A resilient engagement member 78 operates to secure the ligating slide 14 in the closed position. The resilient engagement member 78 is generally L-shaped and includes a lingually-extending prong 80 that is received in a recess 82 formed in support surface 46. The free end of the resilient engagement member 78 is provided with an labially-extending detent or projection 84, which corresponds generally in cross section with the cross section of aperture 76 in ligating slide 14. The projection 84 extends into aperture 76 in ligating slide 14 when ligating slide 14 is in the closed position. The engagement between the projection 84 and the aperture 76 holds the ligating slide 14 in the closed position against movement that would otherwise open the slide 14. As a result, ligating slide 14 is unlikely to be unintentionally moved from the closed position to the opened position.

The free end of resilient engagement member 78 carrying projection 84 is elastically compressed when ligating slide 14 is in an opened position and projection 84 engages the lingual surface of ligating slide 14. Consequently, the free end of resilient engagement member 78 is capable of resiliently flexing or deforming in the labial direction and toward ligating slide 14 when the projection 84 is aligned with aperture 76, for selectively engaging the projection 84 with the aperture 76 so as to lock the ligating slide 14 in the closed position. To that end, resilient engagement member 78 is biased in the labial direction to force projection 84 away from the tooth 23 and toward ligating slide 14.

Figure 4A:
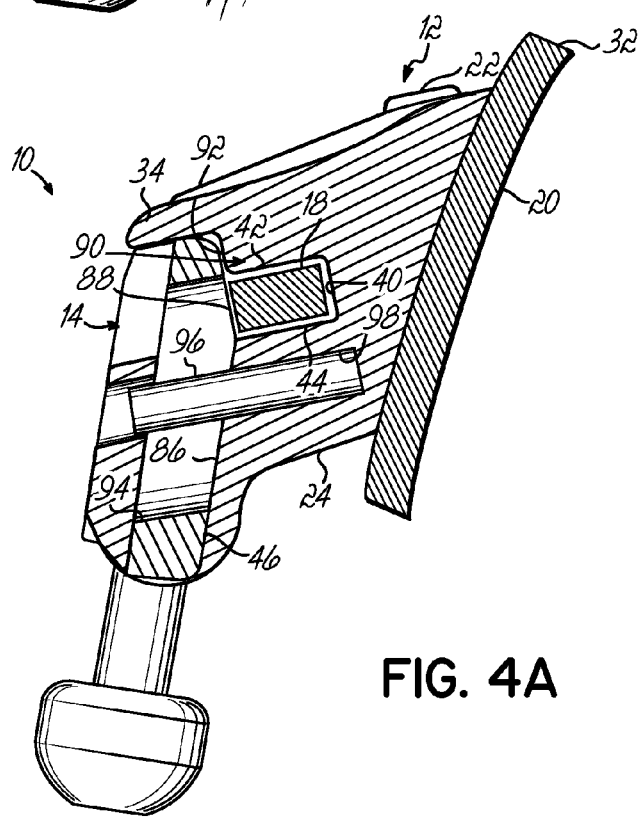
FIG. 4A is a cross-sectional view of the self-ligating orthodontic bracket of FIG. 2 generally taken along line 4A-4A showing a retaining pin in the bracket body and a retaining slot through the ligating slide.
Figure 4B:
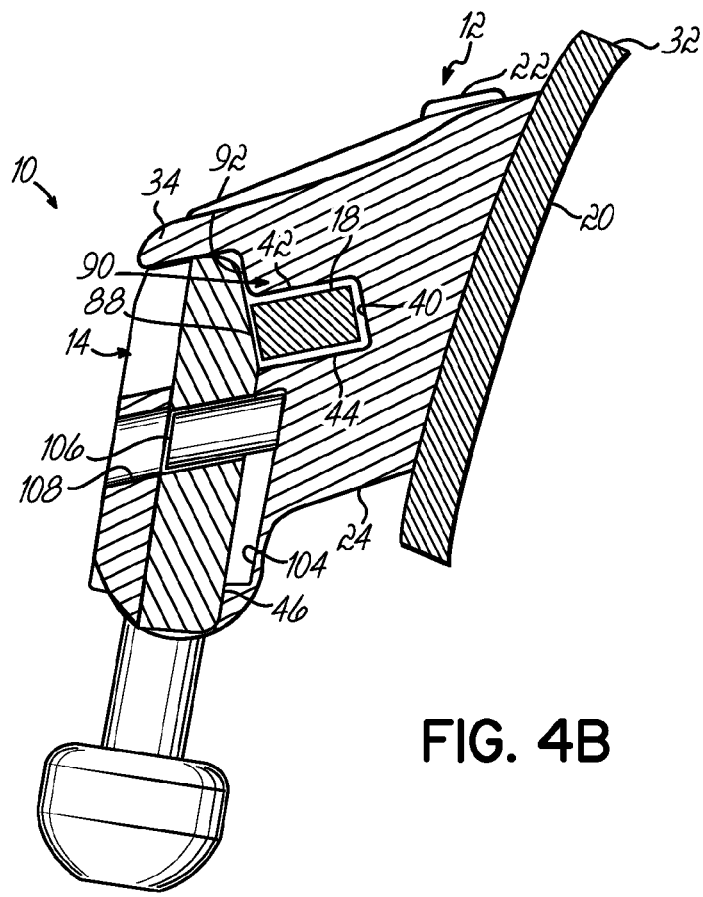
FIG. 4B is a cross-sectional view of an alternate embodiment of the self-ligating orthodontic bracket similar to FIG. 4A showing a retaining groove in the bracket body and a retaining pin in the ligating slide.

In another advantageous aspect of the invention, it is desirable to provide an archwire slot 16 that provides a close fit with the archwire 18 being inserted therein. Thus as shown in FIGS. 3, 4A and 4B, the archwire slot 16 typically has a generally rectangular configuration. The mutual arrangement of the base surface 40 and the side slot surfaces 42, 44 is generally rectangular and provides a close fit to a generally rectangular archwire 18. Nevertheless, because the base plane 58 of the archwire slot 16 and the translation plane 60 along which ligating slide 14 travels are angled with respect to each other, the ligating slide 14 has to be modified in order to provide a close fit to the labial surface of archwire 18. To this end, the lingual surface of slide rails 70, 72 includes a first and second portion 86, 88 respectively. First portion 86 engages the slide grooves 48, 50 of slide engagement track 56. The second portion 88 is angled with respect to first portion 86 such that second portion 88 is generally parallel to base plane 58. Second portion 88 covers the archwire slot 16 when ligating slide 14 is in the closed position. The second portion 88 is angled by an amount substantially equal to the angle A between the base plane 58 and translation plane 60. In this way, ligating slide 14 provides a close fit to the labial surface of archwire 18.

In yet another advantageous aspect of the invention, the labial portion 34 of occlusal side 22 extends in the labial direction beyond the archwire slot 16 to define a ledge, generally shown at 90, extending in the mesial-distal direction. Ledge 90 includes a labial surface 92 that is generally parallel to base plane 58. When the ligating slide 14 is moved to the closed position, the occlusal end of the second portion 88 on slide rails 70, 72 abuts the labial surface 92 of ledge 90 and is covered by labial portion 34 of occlusal side 22. In this way, food or other material in the oral cavity is prevented from contacting the occlusal edge of ligating slide 14 and inadvertently dislodging slide 14 to the opened position. Furthermore, labial portion 34 provides a stop so as to prevent ligating slide 14 from overshooting the closed position as the ligating slide is being moved from the open position to the closed position.

To regulate the movement of the ligating slide 14 relative to bracket body 12, the bracket body 12 may include one of a projecting portion or a receiving portion, and ligating slide 14 may include the other of the projecting portion of the receiving portion. The projecting portion and receiving portion cooperate to regulate the movement of ligating slide 14. For example, as shown in FIG. 4A, ligating slide 14 includes a retaining slot 94 (FIG. 1) through ligating slide 14 and extending generally in the occlusal-gingival direction. Retaining slot 94 may be formed in the distal portion 66 of ligating slide 14, as shown in FIGS. 1 and 2, but may also be formed in the mesial portion 64. A retaining pin 96 includes a lingual portion received within a recess 98 formed in support surface 46 that aligns with the slot 94 in ligating slide 14. The retaining pin 96 projects in the labial direction and is received in slot 94 so that as the ligating slide 14 moves between opened and closed positions, retaining slot 94 moves relative to retaining pin 96, as shown in FIG. 2. The retaining pin/slot configuration prevents accidental or unintentional detachment of the ligating slide 14 from the bracket body 12 during use when the ligating slide 14 is positioned in the opened position. It should be realized that the retaining pin/slot configuration does not lock the ligating slide 14 in any position, as does engagement member 78, but regulates the movement of the ligating slide 14 in the occlusal-gingival direction.

Additionally, the length of retaining slot 94 limits the occlusal-gingival range of movement of ligating slide 14. The retaining slot 94 may be configured lengthwise so that in the fully opened position, the archwire 18 may be inserted into archwire slot 16. For instance, the retaining pin 96 may abut a first slot end 100 when the occlusal edge of ligating slide 14 is approximately flush with archwire slot surface 44. In this way, the archwire 18 may be easily inserted into the archwire slot 16. A second slot end 102 may be configured so that the projection 84 of resilient engagement member 78 is permitted to align with aperture 76 in ligating slide 14 so as to lock the ligating slide 14 in the closed position. Retaining pin 96 may abut second slot end 102 when ligating slide 14 is in the closed position.

An alternate embodiment of the self-ligating orthodontic bracket 10 is shown in FIG. 4B, in which like reference numerals refer to like features in FIG. 4A. In this embodiment, the receiving portion is included on the bracket body 12 and the projecting portion is included on the ligating slide 14. In particular, bracket body 12 includes a retaining groove 104 in the support surface 46 extending generally in the occlusal-gingival direction. The retaining groove 104 may be formed in support surface 46 adjacent the distal side 28 of bracket body 12, but may also be formed adjacent the mesial side 26. A retaining pin 106 includes a labial portion received within a recess 108 in ligating slide 14 that aligns with retaining groove 104 in bracket body 12. The retaining pin 106 projects in the lingual direction and is received in retaining groove 104 so that as the ligating slide 14 moves between opened and closed positions, retaining pin 106 moves relative to retaining groove 104. In operation, the retaining pin/slot configuration shown in FIG. 4B functions in substantially the same manner as the retaining pin/slot configuration shown and described above for FIG. 4A.

Figure 5A:
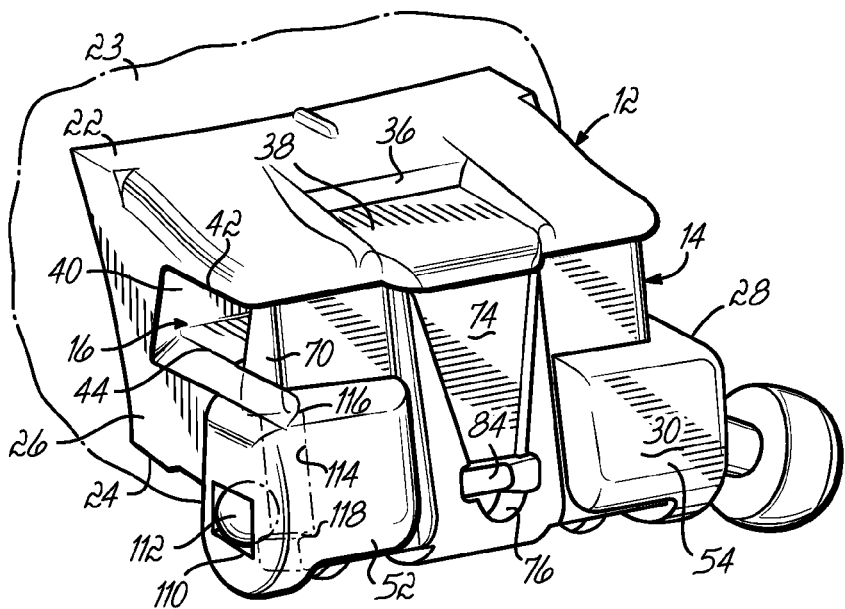
FIG. 5A is a perspective view of an alternate embodiment of the self-ligating orthodontic bracket showing a retaining ball in the bracket body and a retaining groove in the ligating slide.
Figure 5B:
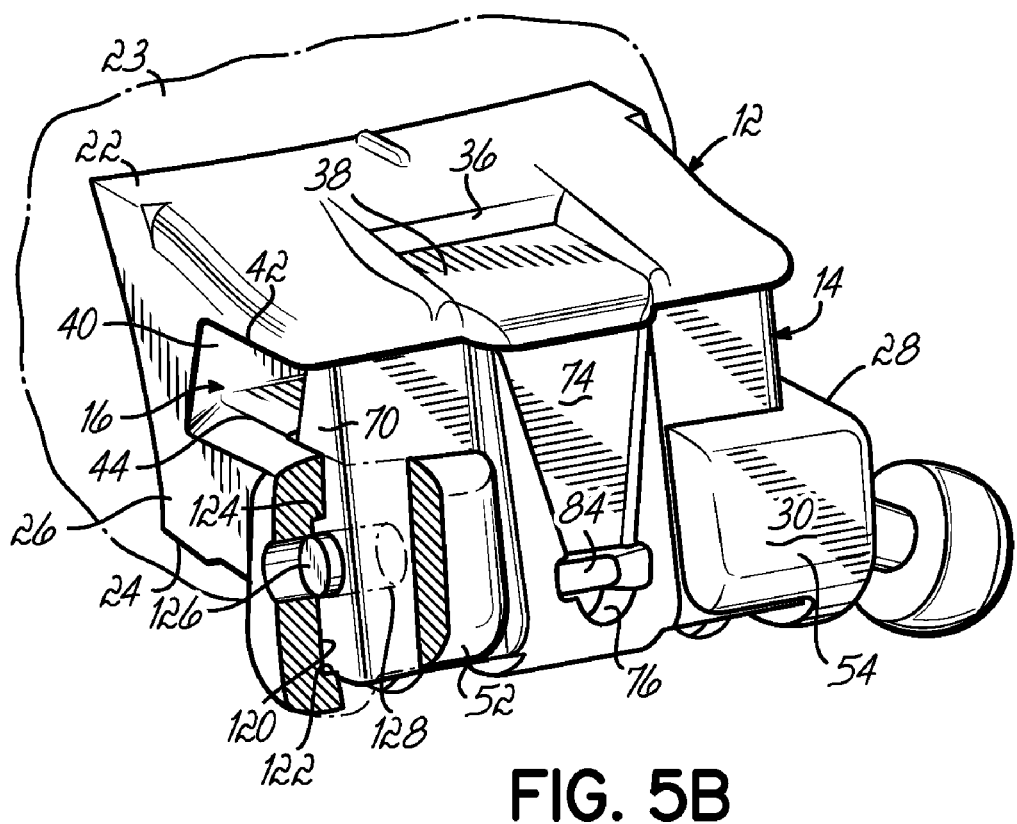
FIG. 5B is a broken away perspective view of an alternate embodiment of the self-ligating orthodontic bracket similar to FIG. 5A showing a retaining groove in the bracket body and a retaining pin in the ligating slide.

In FIGS. 5A and 5B, in which like reference numerals refer to like features in FIGS. 1-4A, the projecting portion and receiving portion have an alternate configuration and/or location for regulating the movement of ligating slide 14 relative to bracket body 12. For example, in the embodiment shown in FIG. 5A, one of the guides, such as guide 52, of bracket body 12 includes an aperture 110 in the mesial side 26 which extends therethrough. A retaining ball 112 is pressed into aperture 110 with an interference fit so that a portion of retaining ball 112 extends into the space between guide 52 and support surface 46. The mesial surface of rail 70 includes a retaining groove 114 (shown in phantom) extending generally in the occlusal-gingival direction and defining a first end and second end 116, 118, respectively. The retaining ball 112 projects in the distal direction and is received in retaining groove 114 so that as ligating slide 14 moves between the opened and closed positions, retaining groove 114 moves relative to retaining ball 112. Those of ordinary skill in the art will recognize that the retaining ball 112 and corresponding retaining groove 114 may also be located in the distal side 28 of bracket body 12 and ligating slide 14.

The retaining ball/groove configuration prevents accidental or unintentional detachment of the ligating slide 14 from bracket body 12 during use when the ligating slide 14 is positioned in the open position and functions in substantially the same manner as the retaining pin/slot configuration shown and described above for FIG. 4A. For instance, the length of retaining groove 114 limits the occlusal-gingival range of movement of ligating slide 14. The retaining groove 114 is configured so that in the fully open position, the archwire 18 may be inserted into archwire slot 16. The retaining ball 112 may abut first groove end 116 when the occlusal end of the ligating slide 14 is approximately flush with archwire slot surface 44. In this way, the archwire 18 may be easily inserted into the archwire slot 16. Furthermore, the second groove end 118 is configured so that the projection 84 of resilient engagement member 78 may be permitted to align with aperture 76 in ligating slide 14 so as to lock the ligating slide 14 in the closed position. Retaining ball 112 may abut second groove end 118 when ligating slide 14 is in the closed position.

Although the embodiment shown in FIG. 5A shows the projecting portion associated with the bracket body 12 and the receiving portion associated with the ligating slide 14, the invention is not so limited as the receiving portion may be associated with the bracket body 12 and the projecting portion may be associated with the ligating slide 14. In the alternate embodiment of the self-ligating orthodontic bracket 10 shown in FIG. 5B, bracket body 12 includes a retaining groove 120 in the distal surface of guide 52 extending generally in the occlusal-gingival direction and defining first and second groove ends 122, 124, respectively. A retaining pin 126 includes a distal portion received within a recess 128 in ligating slide 14 that aligns with retaining groove 120 in guide 52. The retaining pin 126 projects in the mesial direction and is received in retaining groove 120 so that as the ligating slide 14 moves between opened and closed positions, retaining pin 126 moves relative to retaining groove 120. In operation, the retaining pin/slot configuration shown in FIG. 5B functions in substantially the same manner as the retaining ball/groove configuration shown and described above for FIG. 5A.

In these embodiments, the bracket body 12 may be made by any suitable forming technique, such as metal injection molding (MIM), from a biocompatible metal, such as a stainless steel and, more specifically, a 17-4 stainless steel. The resilient engagement member 78 may be made from any suitable material, including stainless steels, titanium alloys and Ni/Ti type superelastic materials. The ligating slide 14 may be formed by any suitable process, such as MIM, from any biocompatible material, including metals such as stainless steel.

With reference to FIG. 2, the ligating slide 14 in the closed position blocks the entrance to the archwire slot 16 to capture the archwire 18 therein and the engagement between projection 84 and aperture 76 provides a latched condition. The ligating slide 14 may be unlocked using an end of a tool (not shown) designed to press the projection 84 inwardly (i.e., lingually) toward the tooth 23 with a force sufficient to overcome the bias applied by resilient member 78 and disengage the projection 84 from the aperture 76 in the ligating slide 14 to provide an unlatched condition. When the projection 84 is moved by the tool inwardly (i.e., lingually) by a distance adequate to substantially clear the plane of the lingual surface of the ligating slide 14, the ligating slide 14 is freely movable using a force applied by the tool occlusal-gingivally toward the opened position in a slideable manner and guided by guides 52, 54. The motion of the ligating slide 14 may be positively stopped in the opened position by contact between the retaining pin 96 and the first slot end 100 of retaining slot 94.

To place the ligating slide 14 in the closed position, slide 14 is moved occlusal-gingivally until the projection 84 springs outwardly under the bias applied by resilient member 78 and is received in the aperture 76. The ligating slide 14 is then securely locked in the closed position. The engagement of the projection 84 into the aperture 76 may create a tactile effect which is perceptible to a clinician and/or emits an audible sound, such as a click, that is likewise perceptible by a clinician. The alternate embodiments shown in FIGS. 4B, 5A and 5B may be operated in a similar manner.

The self-ligating bracket of the invention provides a number of advantages over traditional molar brackets, such as buccal tubes or convertible buccal tubes. In particular, the self-ligating bracket may be used in severely rotated cases without constraining the movement of the archwire. Traditional self-ligating brackets, however, have some problems when applied to molar teeth. The self-ligating bracket of the invention overcomes these limitations. In particular, self-ligating bracket of the invention provides a slide engagement track for the ligating slide that is angled so that the edge of the ligating slide does not contact the gingiva surrounding a molar tooth when the slide is opened. The bracket also provides a contoured-shaped surface that prevents occlusal interference with teeth on the opposite jaw. The bracket further provides a mechanism for regulating the movement of the ligating slide so as to prevent the ligating slide from disengaging from the bracket body.

While the invention has been illustrated by a description of various embodiments and while these embodiments have been described in considerable detail, it is not the intention of the applicant to restrict or in any way limit the scope of the appended claims to such detail. Additional advantages and modifications will readily appear to those skilled in the art. For example, as shown in the figures, the self-ligating orthodontic bracket 10 may include mesial and/or distal hooks that aid in the orthodontic treatment of teeth. The invention in its broader aspects is therefore not limited to the specific details, representative apparatus and methods, and illustrative examples shown and described. Accordingly, departures may be made from such details without departing from the spirit and scope of applicant's inventive concept.

What is claimed is:

1. A self-ligating orthodontic bracket for coupling an archwire with a tooth, comprising:
    a bracket body configured to be mounted to the tooth, the bracket body including a support surface, a ledge, and an archwire slot including a base surface and opposing first and second slot surfaces extending from the base surface, the base surface being interposed between the opposing first and second slot surfaces, the support surface being acutely angled with respect to the base surface, and the ledge opposing the support surface across the archwire slot and including a surface that is generally parallel to the base surface; and
    a movable member coupled with the bracket body and movable between an opened position in which the archwire is insertable into the archwire slot and a closed position in which the movable member retains the archwire in the archwire slot,
    wherein the movable member comprises a first portion and a second portion extending at an acute angle from the first portion, the first portion engaging the acutely angled support surface of the bracket body when the movable member is in the closed position, the second portion being generally parallel to the base surface and extending across the archwire slot from the first slot surface to the second slot surface when the movable member is in the closed position.

2. The self-ligating orthodontic bracket of claim 1, wherein the ledge extends in the mesial-distal direction, the second portion of the movable member cooperating with the ledge when the movable member is in the closed position.

3. The self-ligating orthodontic bracket of claim 1, wherein the support surface is angled between approximately 10 degrees and 25 degrees with respect to the base surface.

4. The self-ligating orthodontic bracket of claim 1, wherein the support surface is angled approximately 20 degrees with respect to the base surface.

5. The self-ligating orthodontic bracket of claim 1, wherein the acute angle between the first portion and the second portion of the movable member is maintained during movement between the opened position and the closed position.

6. The self-ligating orthodontic bracket of claim 1, wherein the support surface intersects one of the opposing first and second slot surfaces to define an edge of the archwire slot and the support surface defines a translation plane that intersects the other of the opposing first and second slot surfaces.

7. The self-ligating orthodontic bracket of claim 1, wherein the second portion of the movable member abuts the surface of the ledge that is generally parallel to the base surface when the movable member is in the closed position.

8. The self-ligating orthodontic bracket of claim 1, wherein a portion of the bracket body that includes the ledge extends beyond the movable member and is configured to prevent food or other material from inadvertently dislodging the member from the closed position.

9. The self-ligating orthodontic bracket of claim 1, wherein a portion of the bracket body that includes the ledge provides a stop to prevent the movable member from overshooting the closed position as the movable member is being moved from the opened position to the closed position.

10. A self-ligating orthodontic bracket for coupling an archwire with a tooth, comprising:
a bracket body configured to be mounted to the tooth, the bracket body including an archwire slot including a base surface and opposing first and second slot surfaces extending from the base surface, the base surface being interposed between the opposing first and second slot surfaces, a support surface being acutely angled with respect to the base surface, and a ledge opposing the support surface across the archwire slot and including a surface that is generally parallel to the base surface; and
a movable member coupled with the bracket body and slidable from a closed position in which the movable member retains the archwire in the archwire slot toward an opened position in which the archwire is insertable into the archwire slot, the movable member comprising a first portion and a second portion extending at an acute angle from the first portion,
wherein the first portion engages the support surface in the closed position and the second portion is generally parallel to the base surface during sliding movement of the movable member from the closed position toward the opened position.

11. The self-ligating orthodontic bracket of claim 10, wherein the movable member further includes an occlusal-gingival extending groove defining at least one end that limits movement of the movable member in at least one direction.

12. The self-ligating orthodontic bracket of claim 11, wherein the first portion defines a plane and the at least one end of the groove defines a projection that defines the end and lies in the plane of the first portion.

13. The self-ligating orthodontic bracket of claim 12, wherein the projection abuts the bracket body when the movable member is in the closed position.

14. The self-ligating orthodontic bracket of claim 10, wherein the second portion extends from the first slot surface to the second slot surface in a direction generally transverse to the archwire slot to cover the archwire slot when the movable member is in the closed position.

15. The self-ligating orthodontic bracket of claim 10, wherein the acute angle between the first portion and the second portion of the movable member is maintained during movement between the opened position and the closed position.

16. The self-ligating orthodontic bracket of claim 10, wherein the support surface intersects one of the opposing first and second slot surfaces to define an edge of the archwire slot and the support surface defines a translation plane that intersects the other of the opposing first and second slot surfaces.

17. A method of using an orthodontic bracket mounted to a tooth surrounded by gingiva, the orthodontic bracket including a bracket body having an archwire slot with a base surface generally defining a base plane, a generally planar support surface acutely angled relative to the base surface, and a ledge opposing the base surface across the archwire slot and including a surface that is generally parallel to the base surface, and a ligating member movably mounted to the bracket body and including a first portion engaging the acutely angled support surface of the bracket body and a second portion extending at an acute angle from the first portion and being generally parallel with the base surface, the method comprising:
moving the ligating member relative to the base plane to an opened position, the archwire slot being accessible when the ligating member is in the opened position and the second portion being generally parallel to the base surface during sliding movement of the ligating member from the closed position toward the opened position;
inserting an archwire into the archwire slot; and
moving the ligating member relative to the base plane to a closed position such that the ligating member engages the acutely angled support surface in the closed position, the archwire being retained in the archwire slot when the ligating member is in the closed position.

18. The method of claim 17, further comprising:
securing the ligating member relative to the bracket body when the ligating member is in the closed position, and
after securing, releasing the ligating member to move the ligating member to the opened position.

19. The method of claim 17, further comprising:
limiting occlusal-gingival movement of the ligating member relative to the bracket body so as to prevent the ligating member from disengaging from the bracket body when the ligating member is moved from the closed position.

20. The method of claim 19, wherein limiting occlusal-gingival movement of the ligating member further comprises:
engaging a projecting portion in one of the bracket body or the ligating member with a receiving portion in the other of the bracket body or the ligating member, the receiving portion having at least one end that stops movement of the projecting portion in one direction.

21. The method of claim 20, wherein the projecting portion includes a retaining pin projecting from the bracket body and the receiving portion includes a retaining slot in the ligating member.

22. The method of claim 20, wherein the projecting portion includes a retaining ball projecting from the bracket body and the receiving portion includes a retaining groove in the ligating member.

23. The method of claim 17, wherein moving the ligating member toward the closed position further comprises:
sliding the first portion in contact with the acutely angled support surface while the second portion remains generally parallel to the base surface during sliding of the ligating member toward the closed position.

24. The method of claim 17, wherein the ligating member further includes an occlusal-gingival extending groove defining at least one end, and wherein moving the ligating member includes limiting occlusal-gingival movement of the ligating member with the end.

25. The method of claim 24, wherein the first portion defines a plane and the at least one end of the groove defines a projection that lies in the plane of the first portion, and wherein regulating occlusal-gingival movement of the ligating member includes sliding the projection into an abutting position against the bracket body when the ligating member is slid to the closed position.

26. A method of using an orthodontic bracket mounted to a tooth surrounded by gingiva, the orthodontic bracket including a bracket body having an archwire slot with a base surface generally defining a base plane, a generally planar support surface acutely angled relative to the base surface, and a ledge opposing the base surface across the archwire slot and including a surface that is generally parallel to the base surface, and a ligating member movably mounted to the bracket body, wherein the ligating member comprises a first portion and a second portion extending at an acute angle from the first portion, the first portion engaging the acutely angled support surface of the bracket body, the method comprising:

sliding the ligating member relative to the base plane toward an opened position, the archwire slot being accessible when the ligating member is in the opened position;

inserting an archwire into the archwire slot; and sliding the ligating member relative to the base plane toward a closed position, the archwire being retained in the archwire slot when the ligating member is in the closed position, wherein, during sliding of the ligating member, the first portion is in contact with the acutely angled support surface while the second portion remains generally parallel to the base surface.

* * * * *